(12) United States Patent
Hirszowicz et al.

(10) Patent No.: US 8,079,978 B2
(45) Date of Patent: Dec. 20, 2011

(54) SPIRAL BALLOON CATHETER

(75) Inventors: Eran Hirszowicz, Ramat Gan (IL); Hila Yaron, Tel Aviv (IL)

(73) Assignee: Intratech Medical Ltd. (IL)

( * ) Notice: Subject to any disclaimer, the term of this patent is extended or adjusted under 35 U.S.C. 154(b) by 0 days.

(21) Appl. No.: 12/822,865

(22) Filed: Jun. 24, 2010

(65) Prior Publication Data

US 2010/0262124 A1    Oct. 14, 2010

Related U.S. Application Data

(62) Division of application No. 12/078,191, filed on Mar. 27, 2008, now Pat. No. 7,766,871.

(60) Provisional application No. 60/920,145, filed on Mar. 27, 2007, provisional application No. 60/978,122, filed on Oct. 7, 2007, provisional application No. 61/038,795, filed on Mar. 24, 2008.

(51) Int. Cl.
*A61M 31/00* (2006.01)

(52) U.S. Cl. .................................. 604/103.07

(58) Field of Classification Search ............. 604/103.07
See application file for complete search history.

(56) References Cited

U.S. PATENT DOCUMENTS

| | | | |
|---|---|---|---|
| 4,762,130 A * | 8/1988 | Fogarty et al. ............. | 606/159 |
| 5,295,959 A | 3/1994 | Gurbel et al. | |
| 5,308,356 A | 5/1994 | Blackshear, Jr. et al. | |
| 5,383,856 A | 1/1995 | Bersin | |
| 5,395,333 A | 3/1995 | Brill | |
| 5,484,411 A | 1/1996 | Inderbitzen et al. | |
| 5,545,132 A | 8/1996 | Fagan et al. | |
| 5,735,816 A | 4/1998 | Lieber et al. | |
| 5,749,852 A * | 5/1998 | Schwab et al. .......... | 604/103.01 |
| 5,759,172 A | 6/1998 | Weber et al. | |
| 5,797,877 A | 8/1998 | Hamilton et al. | |
| 5,797,948 A | 8/1998 | Dunham | |
| 5,814,064 A | 9/1998 | Daniel et al. | |
| 5,855,546 A | 1/1999 | Hastings et al. | |
| 5,871,475 A | 2/1999 | Frassica | |
| 5,891,386 A | 4/1999 | Deitermann et al. | |
| 5,954,740 A | 9/1999 | Ravenscroft et al. | |
| 6,053,932 A | 4/2000 | Daniel et al. | |
| 6,129,706 A | 10/2000 | Janacek | |
| 6,190,356 B1 | 2/2001 | Bersin | |
| 6,245,089 B1 | 6/2001 | Daniel et al. | |

(Continued)

FOREIGN PATENT DOCUMENTS

EP    0834333 A1    4/1998

(Continued)

OTHER PUBLICATIONS

U.S. Appl. No. 60/920,145, filed Mar. 27, 2007, Hirszowicz et al.

(Continued)

*Primary Examiner* — Nicholas Lucchesi
*Assistant Examiner* — Diva Ranade
(74) *Attorney, Agent, or Firm* — Patton Boggs LLP

(57) ABSTRACT

The present invention provides a balloon catheter system comprising one or more conduits to which are attached a compliant balloon having a non-helical shape in its deflated state, wherein said balloon is constructed such that is capable of adopting a spiral or helical conformation upon inflation. In addition, the present invention also provides methods for using said balloon catheter system.

20 Claims, 8 Drawing Sheets

U.S. PATENT DOCUMENTS

| | | | |
|---|---|---|---|
| 6,340,364 B2 * | 1/2002 | Kanesaka | 606/200 |
| 6,350,271 B1 | 2/2002 | Kurz et al. | |
| 6,443,926 B1 | 9/2002 | Kletschka | |
| 6,450,988 B1 | 9/2002 | Bradshaw | |
| 6,478,807 B1 | 11/2002 | Foreman et al. | |
| 6,527,739 B1 | 3/2003 | Bigus et al. | |
| 6,663,652 B2 * | 12/2003 | Daniel et al. | 606/200 |
| 6,679,860 B2 | 1/2004 | Stiger | |
| 6,716,236 B1 * | 4/2004 | Tzeng et al. | 607/105 |
| 6,743,196 B2 | 6/2004 | Barbut et al. | |
| 6,881,216 B2 | 4/2005 | Di Caprio et al. | |
| 6,896,842 B1 | 5/2005 | Hamilton et al. | |
| 6,923,808 B2 | 8/2005 | Taimisto | |
| 7,081,115 B2 | 7/2006 | Taimisto | |
| 7,122,003 B2 | 10/2006 | Nakao | |
| 7,144,408 B2 * | 12/2006 | Keegan et al. | 606/200 |
| 7,244,242 B2 * | 7/2007 | Freyman | 604/96.01 |
| 7,457,661 B2 | 11/2008 | Doty | |
| 7,462,175 B2 | 12/2008 | Chang et al. | |
| 7,465,291 B2 | 12/2008 | Massengale | |
| 7,491,188 B2 | 2/2009 | Holman et al. | |
| 2004/0006341 A1 | 1/2004 | Shaolian et al. | |
| 2004/0236310 A1 | 11/2004 | Chin et al. | |
| 2005/0171572 A1 | 8/2005 | Martinez | |
| 2005/0177130 A1 | 8/2005 | Konstantino et al. | |
| 2005/0228417 A1 * | 10/2005 | Teitelbaum et al. | 606/159 |
| 2006/0259005 A1 | 11/2006 | Konstantino et al. | |
| 2006/0276820 A1 | 12/2006 | Yamaguchi et al. | |
| 2008/0125798 A1 | 5/2008 | Osborne et al. | |
| 2008/0167678 A1 | 7/2008 | Morsi | |
| 2008/0306440 A1 | 12/2008 | Hirszowicz et al. | |
| 2010/0114022 A1 | 5/2010 | Hirszowicz et al. | |
| 2010/0137793 A1 | 6/2010 | Hirszowicz et al. | |

FOREIGN PATENT DOCUMENTS

| | | |
|---|---|---|
| WO | WO-93/17748 | 9/1993 |
| WO | WO-2008/117256 | 10/2008 |
| WO | WO-2008/117257 | 10/2008 |

OTHER PUBLICATIONS

U.S. Appl. No. 60/978,122, filed Oct. 7, 2007, Hirszowicz et al.
U.S. Appl. No. 61/038,795, filed Mar. 24, 2008, Hirszowicz et al.
In the U.S. Patent and Trademark Office, Restriction Requirement in re: U.S. Appl. No. 12/078,191, dated Jul. 22, 2009, 7 pages.
In the U.S. Patent and Trademark Office, Non-Final Office Action in re: U.S. Appl. No. 12/078,191, dated Oct. 6, 2009, 6 pages.
In the U.S. Patent and Trademark Office, Non-Final Office Action in re: U.S. Appl. No. 12/078,191, dated Mar. 24, 2010, 5 pages.
International Search Report, Written Opinion & International Preliminary Report on Patentability dated Dec. 10, 2008, for PCT No. PCT/IB2008/051160.
International Search Report, Written Opinion & International Preliminary Report on Patentability dated Dec. 10, 2008, for PCT No. PCT/IB2008/051158.

* cited by examiner

SPIRAL BALLOON CATHETER

CLAIM FOR PRIORITY

This application is a divisional of U.S. application Ser. No. 12/078,191, filed Mar. 27, 2008, which claims priority to U.S. Provisional Application No. 60/920,145, filed Mar. 27, 2007, U.S. Provisional Application No. 60/978,122, filed Oct. 7, 2007 and U.S. Provisional Application No. 61/038,795, filed Mar. 24, 2008, the contents of which are herein incorporated by reference in their entireties.

FIELD OF THE INVENTION

The present invention relates to a balloon catheter device for use inside blood vessels and other body passages. More specifically, the presently-disclosed invention is a catheter device comprising a balloon that is capable of adopting a spiral conformation upon inflation.

BACKGROUND OF THE INVENTION

Balloon catheters have, over the course of the last few decades, found use in the diagnosis and treatment of many medical conditions. While different versions of these devices have been designed and constructed for use in many different body passages—such as the urinary tract, uterus and fallopian tubes and gastrointestinal tract—the intravascular use of balloon catheters is arguably their fastest-growing field of application. Thus, balloon catheters have been used in various angioplasty procedures, stent implantation, thrombus-crossing, embolic protection, and so on.

The inappropriate and undesirable formation of blood clots intravascularly may have severe pathological consequences, as a consequence of the disturbance of blood flow to vital organs and tissues such as the heart muscle and brain. In extreme cases, total occlusion of the afferent arteries may lead to ischemic damage which, in the case of the heart, may manifest itself clinically in the form of myocardial infarction. Similarly, the local production of thrombi in the cerebral vessels or the deposition therein of thrombotic emboli may lead to cerebral infarcts. In both cases, serious morbidity and death are common consequences. It has been estimated, for example, that emboli arising from atherosclerotic plaques of the carotid artery cause approximately one quarter of the 500,000 strokes that are recorded annually in the United States.

Several different medical and surgical approaches aimed at removing thrombotic and embolic material from blood vessels have been proposed and attempted. One such approach requires the injection of thrombolytic agents. Alternatively or additionally, a variety of balloon catheter systems have been used to both expand blood vessels that have become narrowed due to thrombus formation or deposition and, in some cases to collect detached thrombotic material and remove same from the body.

One example of a balloon catheter system that has been designed for use in removing thrombotic material and other intravascular particulate matter from the body is that disclosed in U.S. Pat. No. 4,762,130 (Fogarty). While several different embodiments of the catheter are described in the patent, a feature common to all of these embodiments is that a balloon is advanced into the region of the thrombus to be treated and then expanded into a helical or spiral configuration, thereby engaging said thrombus within the spiral channels of the inflated balloon. The spiral balloon is then withdrawn from the body with the thrombus still attached thereto.

A particular disadvantage of this prior art system is that the catheter is usually inflated distally to the thrombus (or other particulate matter) and is then pulled back in order to facilitate collection of the thrombotic material by the balloon. This procedure can be traumatic for the blood vessel. Furthermore the balloon does not always completely seal the vessel and some of the debris escapes into the blood stream and is not removed.

A further key problem associated with the aforementioned prior art system is the fact that during balloon inflation, the blood flow through the vessel is blocked. Indeed, in many balloon catheter systems, the volume taken up by the balloon when inflated is problematic. In addition, many existing catheter balloons, even when in their deflated state present an unacceptably large cross-sectional profile, thereby causing problems in the insertion and maneuvering of the catheter within the vasculature.

It is a purpose of the present invention to provide a novel balloon catheter system that presents both a small cross-sectional profile when the balloon is deflated, and which allows blood flow therearound, even when the balloon is fully inflated.

It is a further purpose of the invention to provide a system that may be used for trapping and retaining particulate matter and safely removing said matter from the body.

It is a still further purpose of the invention to provide a balloon catheter system that overcomes the problems and disadvantages associated with prior art devices.

Further objects and advantages of the present invention will become apparent as the description proceeds.

SUMMARY OF THE INVENTION

The present inventors have unexpectedly discovered that compliant tubes (i.e. balloons or sheaths) that fulfill certain dimensional criteria may be caused to adopt a spiral or helical conformation when expanded. In contradistinction to certain prior art balloons, the compliant tubes of the present invention are able to adopt spiral conformations upon inflation without the need for any additional structural features such as external restraining bands or intraluminal spiral-forming wires. In other words, the balloons of the present invention have an intrinsic ability to adopt a spiral shape upon inflation, said ability being a function of the materials used in the construction of the balloon, the dimensions of the balloon, and the attachment of the balloon at each of its ends to a catheter shaft. This novel form of compliant balloon has significant advantages in relation to prior art balloons, in terms of possessing both an extremely low cross sectional profile when deflated, and a helical or spiral shape when inflated.

The present invention, in its most general form, is a balloon catheter device comprising a tubular compliant balloon that is attached at its distal and proximal extremities to a catheter tube. Upon inflation, the balloon, which is incapable of any significant elongation in a proximal-distal direction (due to its terminal attachment to the catheter shaft), adopts a spiral or helical conformation. It is to be emphasized that in its deflated state, the balloon appears as a conventional, low profile, linear (i.e. non-spiral) sheath surrounding the conduit to which it is attached. It is only during inflation that this linear sheath adopts a spiral conformation.

The present invention is therefore primarily directed to a balloon catheter system comprising one or more conduits to which is/are attached a compliant balloon having a non-helical shape in its deflated state, wherein said balloon is constructed such that upon inflation, it is capable of adopting a spiral or helical conformation, and wherein said balloon does not require the use of any ancillary structures such as wires, bands or formers in order to adopt said helical shape upon inflation.

For the purposes of the present disclosure, the terms "proximal" and "distal" are defined from the physician's (or other operator's) perspective. Thus, the term "proximal" is used to refer to the side or end of a device or portion thereof that is closest to the external body wall and/or the operator, while the term "distal" refers to the side or end of a structure that is in an opposite direction to the external body wall and/or operator.

In one preferred embodiment the distal and proximal necks of the balloon are attached to a single catheter conduit. In another preferred embodiment, the distal neck of the balloon is attached to one catheter conduit while the proximal neck thereof is attached to a second conduit, wherein said first and second conduits are arranged such that at least a portion of the shaft of one of the conduits is disposed within the lumen of the other conduit.

In another preferred embodiment, the balloon catheter system further comprises an aspiration element. The general form of this element is a low-profile suction tube, the proximal end of which is connected to a negative pressure source, and the open distal end of which is located close to the proximal neck of the balloon. Preferably, the aspiration element is bound to the catheter conduit.

In another aspect, the present invention is directed to a method for removing particulate matter from a body passage in a patient in need of such treatment, comprising the steps of:
a) providing a catheter fitted with a compliant balloon and an aspiration element, as disclosed hereinabove, wherein said balloon is constructed such that it has a non-spiral shape when deflated and adopts a spiral conformation when inflated;
b) introducing said catheter into a peripheral blood vessel and advancing same until said balloon is located in the region of the particulate matter to be removed;
c) inflating said balloon such that it adopts a spiral conformation having a spiral channel winding around the external surface of said balloon, thereby causing said particulate matter to enter said spiral channel and to becomes squeezed and elongated between said balloon and said blood vessel wall;
d) aspirating said squeezed particulate matter into said aspiration element, wherein said aspiration may be performed continuously or intermittently;
e) optionally partially or completely deflating the balloon and re-locating the catheter such that said balloon becomes located in another region of particulate matter to be removed, and repeating steps (c) and (d);
f) completely deflating the balloon and withdrawing the catheter from the patient's vasculature.

In one preferred embodiment of this method, the particulate matter to be removed is thrombotic or embolic in origin.

The present invention also provides a method for removing thrombotic material from a body passage in a patient in need of such treatment, comprising the steps of:
a) providing a catheter fitted with a compliant balloon, as disclosed hereinabove, wherein said balloon is constructed such that it has a non-spiral shape when deflated and adopts a spiral conformation when inflated;
b) introducing said catheter into a peripheral blood vessel and advancing same until said balloon is located in the region of the thrombotic material to be removed;
c) inflating said balloon such that it adopts a spiral conformation having a spiral channel winding around the external surface of said balloon, thereby causing said thrombotic material to enter said spiral channel and to becomes squeezed and elongated between said balloon and said blood vessel wall;
d) deflating said balloon, thereby creating a space between the deflated balloon and the squeezed thrombotic material, into which a thrombolytic agent may be introduced, thereby enhancing thrombo-dissolution;
e) rapidly repeating steps (c) and (d); and
f) completely deflating the balloon and withdrawing the catheter from the patient's vasculature.

The present invention further provides a method for removing a thrombus from a body passage in a patient in need of such treatment, comprising the steps of:
a) providing a catheter fitted with a compliant balloon, as disclosed hereinabove, wherein said balloon is constructed such that it has a non-spiral shape when deflated and adopts a spiral conformation when inflated;
b) introducing said catheter into a peripheral blood vessel and advancing same until said balloon is located in the region of the thrombus to be removed;
c) trapping the thrombus within the spiral channel formed by inflation of the balloon
d) withdrawing the catheter through the vasculature and out of the body, together with said entrapped thrombus.

In another aspect, the present invention also provides a balloon catheter system comprising one or more conduits to which is/are attached an inner compliant balloon having a non-helical shape in its deflated state and an outer non-compliant or semi-compliant balloon, such that said inner balloon is enclosed by said outer balloon, and wherein the inner balloon is constructed such that upon inflation, said inner balloon is capable of adopting a spiral or helical conformation. The catheter system is further characterized in that the outer balloon is perforated by a first set of pores or openings along most or all of its surface, and is further perforated by a second set of pores or openings in the regions of the proximal neck or taper of said outer balloon, wherein the pores or openings of said second set are significantly fewer in number and larger in diameter than said first set.

In one preferred embodiment the distal and proximal necks of the inner and outer balloons are attached to a single catheter conduit. In another preferred embodiment, the distal necks of the inner and outer balloons are attached to one catheter conduit while the proximal necks thereof are attached to a second conduit, wherein said first and second conduits are arranged such that at least a portion of the shaft of one of the conduits is disposed within the lumen of the other conduit.

In another embodiment of the device of the invention, said device further comprises a layer of an absorbent material surrounding the tubular shaped inner balloon in an annular manner. While any suitable absorbent material may be used for this purpose, in a preferred embodiment, said material is selected from the group consisting of steel wool and fibrous polymers. Unlike the embodiments of the device described hereinabove, the presently-disclosed device does not have an open spiral channel when the inner balloon is inflated. Rather, said spiral channel is obliterated by the present of the absorbent material. Thus, rather than trapping particulate matter within the spiral channel as described above, in the presently-disclosed embodiment, the thrombotic debris and/or other matter is absorbed within the pores of the absorbent layer.

In another aspect, the present invention is directed to a method for removing particulate matter from a body passage in a patient in need of such treatment, comprising the steps of:
a) providing a catheter fitted with an inner compliant balloon and an outer semi-compliant or non-compliant balloon as disclosed hereinabove, wherein the outer balloon is perforated by a first set of pores or openings along most or all of its surface, and is further perforated by a second set of pores or openings in the regions of the proximal neck or taper of said outer balloon, wherein the pores or openings of said second set are significantly fewer in number and larger in diameter than those of said first set;

b) introducing said catheter into a peripheral blood vessel and advancing same until the balloons are located in the region of the particulate matter to be removed;

c) partially inflating the inner balloon to a first expanded state such that the inner balloon adopts a spiral conformation and such that a spiral channel is formed between said spiral balloon and the outer balloon, said channel becoming filled with particulate matter that has entered said spiral channel through the aforementioned second set of pores located in the region of the proximal neck of said outer balloon;

d) further inflating the inner balloon to a second expanded state, such that the proximal coils of the spiral-shaped inner balloon block the aforementioned openings in the outer balloon and reduce the volume of the spiral channel formed in step (c), thereby causing the outward passage of particulate matter of a size smaller than the average diameter of the first set of pores through said pores, but retaining particulate matter of particulate matter of a size larger than said average diameter in the reduced space between the inner and outer balloons;

e) partially deflating the inner balloon to the aforementioned first expanded state such that further particulate matter may be received in the spiral channel;

f) repeating steps (d) and (e) as required until sufficient particulate matter has been accumulated in the space between the inner and outer balloons; and g) completely deflating the inner balloon and withdrawing the catheter from the patient's vasculature with the particulate matter trapped between the inner and outer balloons.

In the above-described method, the phrase "in the region of the particulate matter to be removed" is intended to convey the meaning that the balloons may be located at any of the following locations: entirely proximal to the debris, entirely distal to the debris, entirely within the region of the debris or partially within and partly without (distal or proximal to) the region of the debris.

Although the method defined hereinabove may be used to remove many different types of particulate matter from blood vessels and other body passages, in a preferred embodiment, said particulate matter is thrombotic material.

All the above and other characteristics and advantages of the present invention will be further understood from the following illustrative and non-limitative examples of preferred embodiments thereof.

DETAILED DESCRIPTION OF PREFERRED EMBODIMENTS

The invention is based on the use of a compliant balloon which is fitted over a catheter conduit in a conventional (i.e. non-spiral) and manner, the distal and proximal ends of said balloon being attached to said conduit.

Figure 1:
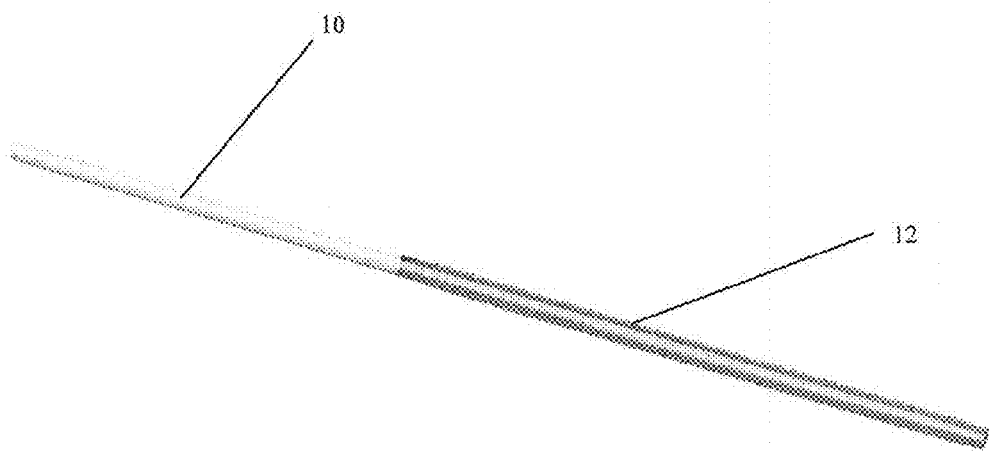
FIG. 1 depicts the balloon catheter of the present invention with the compliant balloon in its collapsed, deflated state.

In its deflated state (FIG. 1), the balloon is in the form of a tube of compliant material with a diameter, in one preferred embodiment, of up to $1/15$ of the final crossing profile of the inflated balloon. The tube can be constructed with a uniform wall thickness or with a wall thickness which varies along its length. The collapsed balloon is indicated in FIG. 1 by part number 12 attached to catheter shaft 10.

The balloon can be made from one material. Alternatively, it may be constructed from two or more different materials, thereby producing a non-uniform spiral balloon upon inflation. Suitable materials for use in constructing the compliant balloon include (but are not limited to): silicones and thermoplastic elastomers (TPEs) such as (but not limited to) Evoperene and Monoprene. The balloon may be manufactured from these materials using standard balloon production techniques well known to the skilled artisan in this field.

The balloon 12 is bound at two points to a rigid or semi-rigid conduit 10 which is threaded through the balloon. Since the balloon is made of a compliant material it elongates during inflation. The attachment of the balloon to the catheter conduit may be achieved using any of the standard bonding techniques and materials well known in the art, for example adhesion using biocompatible glues such as silicone glue.

Figure 2:
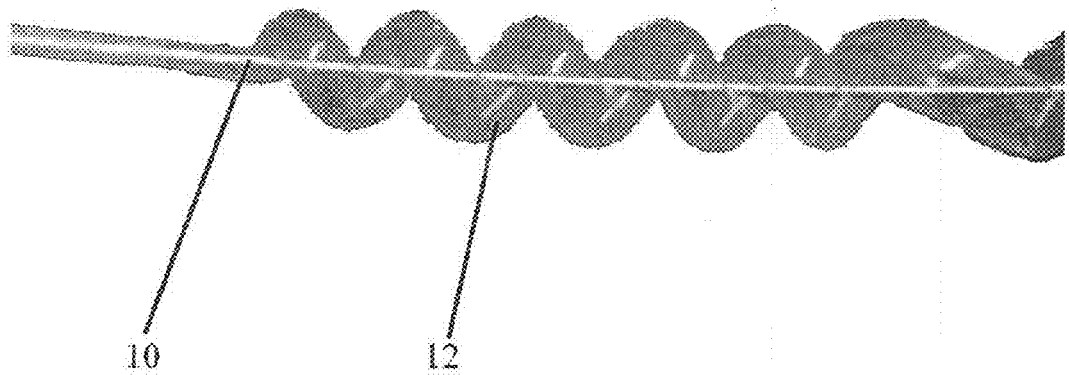
FIG. 2 illustrates the catheter of the present invention following inflation of the balloon.

Since the balloon 12 is bound at both its ends, its longitudinal elongation is restrained. Provided certain balloon-related design parameter criteria are met (as will be discussed hereinbelow), said balloon 12 will then buckle and assume a spiral shape as shown in FIGS. 2 and 3.

Figure 3:
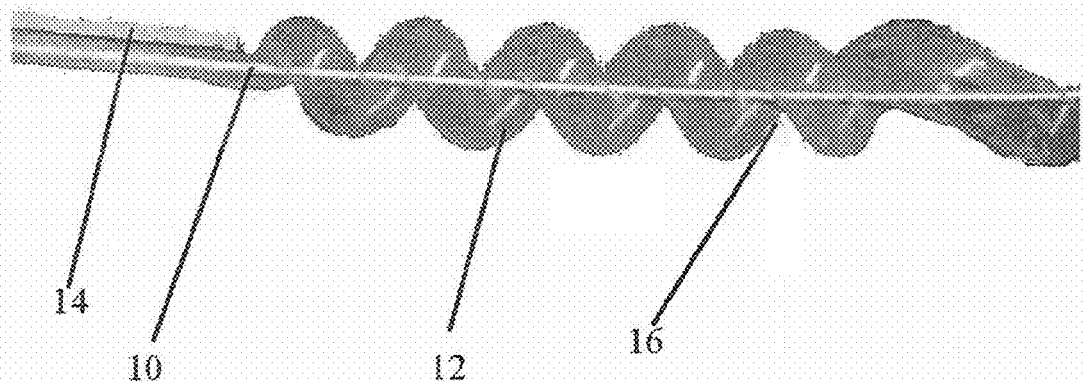
FIG. 3 illustrates one preferred embodiment of the balloon catheter of the present invention having an aspiration element that ends on the proximal side of the balloon (shown inflated).

FIG. 3 illustrates a preferred embodiment of the balloon catheter which further comprises an aspiration element 14. The general form of this element is a low-profile suction tube, the proximal end of which is connected to a negative pressure source, and the open distal end of which is located close to the proximal neck of the balloon. In one embodiment, the aspiration element is bound to the catheter conduit by means of loops, ties or any other suitable method. Alternatively, the aspiration element may be unattached to the catheter conduit. The aspiration tube may be made from any suitable biocompatible material such as (but not limited to) Pebax and Nylon. Typically, the aspiration tube may have an external diameter of 6Fr and an internal diameter of 0.070". However, it is also possible to use larger or smaller tubes to achieve the same result, and without deviating from the scope of the present invention.

Typical aspiration pressures are in the order of 640 to 680 mmHg, and may be provided by standard negative pressure sources such as are available in hospitals and other healthcare centers.

FIG. 3 also illustrates that when compliant balloon 12 is inflated, a spiral channel 16 is formed. The presence of this channel is advantageous for at least two reasons. Firstly, the presence of the open channel prevents occlusion of the blood vessel when the balloon is fully inflated. Secondly, in some embodiments of the invention, the spiral channel may be used for the capture and removal of particulate matter (e.g. thrombotic material) from the blood vessel.

The embodiment of the device illustrated in FIG. 3 is capable of removal of a large thrombus from vessels using a low profile catheter that can be introduced into the body using a 5-Fr introducer. In general terms, thrombus removal is achieved by altering the thrombus shape (e.g. by causing elongation and flattening thereof) so that it can be easily aspirated through the low profile aspiration tube and thereby removed from the body. A method for removing particulate matter from body passages (for example—thrombus material from blood vessels) will be described in more detail hereinbelow.

It has been unexpectedly found by the present inventors that certain fundamental conditions need to exist in order for the compliant balloon of the present invention to adopt a spiral or helical shape when inflated. These may be summarized as follows:
1. For a specific balloon dimension the balloon material should have a minimum value of elongation (E).
2. For a given specific balloon dimension and a specific elongation of the material a minimum initial length of tube ($L_0$) is necessary.
3. The compliant balloon tube should be assembled on a rigid or semi-rigid core shaft that withstands the longitudinal spiral forces. Otherwise the core shaft will elongate and the spiral balloon will become a spherical balloon.
4. The balloon tube should be attached at both ends to the rigid core shaft so that its longitudinal elongation is restricted.
5. Minimum radial uniformity of the wall thickness of the balloon tube is necessary to form a spiral balloon.
6. Minimum homogeneity of the balloon material is necessary to form a spiral balloon.
7. The space between the outer surface of the shaft and the inner wall of the compliant tube ("t") should allow relative movement of the compliant tube over the core shaft during inflation. If the space is too small or non-existent, the friction between the balloon and the shaft does not allow an even elongation of the tube and the formation of a spiral shape.

Figure 4:
FIG. 4 is a schematic longitudinal section view of a balloon catheter of the present invention in its deflated state, in which various critical balloon design parameters are defined.
Figure 5:
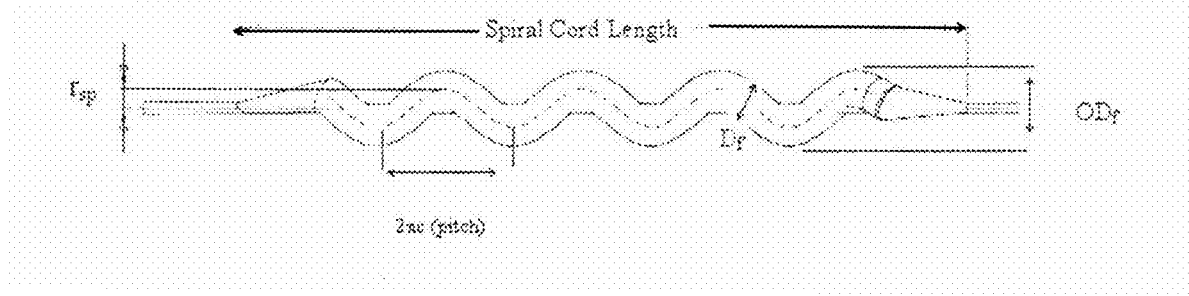
FIG. 5 is a schematic longitudinal section view of a balloon catheter of the present invention in its inflated state, in which various critical balloon design parameters are defined.

The critical balloon and catheter tube parameters (including those mentioned above), are defined in FIG. 4 (deflated state) and FIG. 5 (inflated state), and in the following list:

Spiral Arc is the guideline of the inflated spiral balloon which is measured along the center line of the inflated balloon Spiral Cord is the straight line going from the start point to the end point of the spiral arc E is the elongation fraction of the balloon upon inflation (depends on the material elasticity)

$L_0$ is the length of the balloon in its deflated state $L_f$ is the length of the inflated balloon if allowed to inflate longitudinally, equals $L_0(1+E)$ $D_0$ is the inner diameter of the deflated balloon $OD_0$ is the outer diameter of the deflated balloon $D_f$ is the diameter of the inflated tube, equals $D_0(1+E)$ $OD_f$ is the diameter of the inflated spiral balloon N is the number of threads of the spiral balloon $2\pi C$ is the vertical separation of the spiral threads (pitch)

$r_{spiral}$ is the radius of the spiral arc of the inflated balloon $L_{spiral}$ is the length of the spiral arc of the inflated balloon Only when the conditions defined above are met will a non-spiral compliant balloon adopt a spiral conformation upon inflation. Following extensive investigations of the relevant parameters, the inventors have succeeded in defining the conditions for spiral formation of the balloons of the present invention in formal terms. This formal definition may be summarized in the following expression:

$$N = \sqrt{\frac{L_0^2}{\pi^2 D_0^2} - \frac{L_0^2}{\pi^2 D_0^2 (1+E)^2}} = \sqrt{\frac{L_0^2 E(2+E)}{\pi^2 D_0^2 (1+E)^2}} \geq 2$$

Clearly, N (the number of spiral threads) needs to have a value of at least two in order for a spiral structure to be formed upon inflation. Thus, in accordance with this formal definition, in order for a compliant balloon of the present invention (bound at both of its ends to a rigid catheter shaft) to adopt a spiral conformation upon inflation, it is necessary for the relative values of Lo, E and Do (all as defined above) to be such that N has a value of at least two.

Examples of various compliant tubular balloons and their ability to adopt a spiral conformation are summarized in the Example provided hereinbelow.

Using different wall thicknesses or different materials the shape of the helix and the inflation sequence can be controlled. In one preferred embodiment, for example, it has been found that a compliant balloon having a length of 30 mm, an outer diameter of 1 mm and a wall thickness of 0.25 mm readily adopts a spiral conformation upon inflation, provided that both ends of said balloon are bound to a rigid conduit.

Typically, the compliant balloon will have a length in the range of 15 mm to 50 mm and a wall thickness in the range of 100 micron to 400 micron. It should be emphasized that the preceding dimensions (and all other dimensions that appear herein) are exemplary values only, and should not be construed as limiting the size of the presently-disclosed device in any way.

The general embodiment of the balloon catheter of the present invention that is described hereinabove and depicted in FIGS. 1 to 3 comprises a single catheter conduit to which the compliant balloon is attached. However, it is to be recognized that many other catheter conduit conformations may also be used in the present invention. For example, instead of the single-conduit system, the device of the present invention may have a two-conduit conformation, with (for example) the proximal neck of the balloon being attached to the outer surface of an outer conduit, while the distal neck thereof is attached to the outer surface of an inner conduit that is disposed within the lumen of said outer conduit. In this type of conformation, the inner conduit will generally extend beyond the distal end of the outer conduit. The device of the present invention may also comprise one or more conduits having multiple lumens (e.g. bi-lumen catheters) where the additional lumens may be used for a variety of purposes, including the passage of guidewires, instrumentation or tools.

Figure 6:
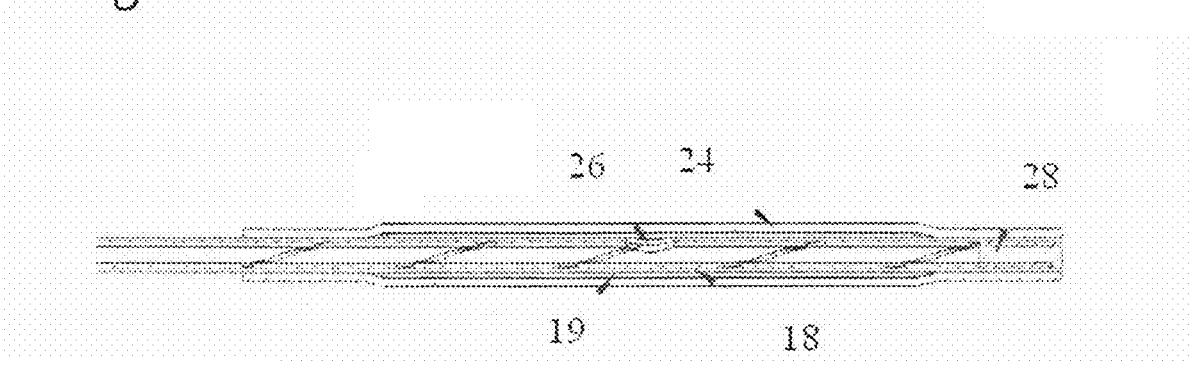
FIG. 6 shows a longitudinal section of a spiral-forming balloon (deflated) mounted on a single-lumen stainless steel tube.

In addition, various catheter tubes having a particularly small cross-sectional profile may be used to mount the spiral-forming balloon of the present invention. In one preferred embodiment of this type of device, the catheter is constructed of a single-lumen stainless steel tube with a distally assembled spiral balloon (FIG. 6). The deflated cross profile ranges between 0.4 and 0.8 mm. The tube may be delivered to the target through a 2.4 Fr or 3.8 Fr microcatheter. The catheter tube 18 can have a laser cut (spiral cut or grooves) at its distal section or all along its length to increase its flexibility. In order to maintain the integrity of the lumen, a thin (approximately 0.0005") polymeric jacket 19 (for example, PET or PTFE) is applied over the tube (e.g. by a heat-shrink process). An aperture 26 is created at the distal section of the hypotube for the inflation of the spiral balloon. The distal end of the hypotube 28 is plugged by using a plasma weld process, laser weld process or adhesive process. The compliant balloon 24 is shown in this figure and in the figures that follow in its deflated state.

The aforementioned spiral-forming balloon 24 is attached at its ends to the distal portion of the hypotube (in a non-spiral, conventional manner) by means of thermo-bonding or adhesive technology.

Figure 7:
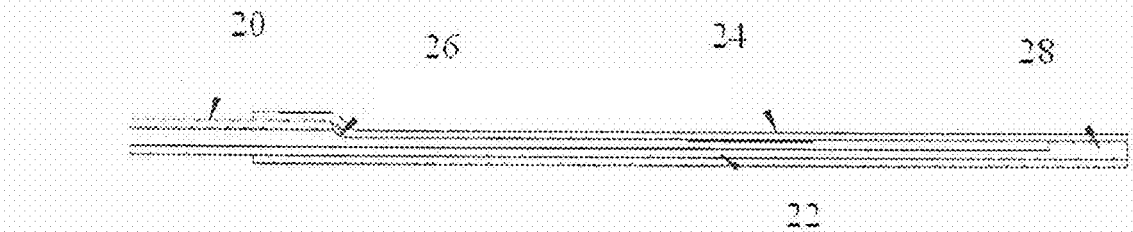
FIG. 7 shows a longitudinal section of a spiral-forming balloon (deflated) mounted on a guidewire state having a sliced distal portion.

In a variant of this embodiment, shown in FIG. 7, a reduced cross-section profile of the distal portion of the hypotube 20 (i.e. in the region of the balloon attachment) is obtained by longitudinally slicing said portion, thereby creating a reduced diameter tube region 22 of approximately semi-circular cross sectional form.

Figure 8:
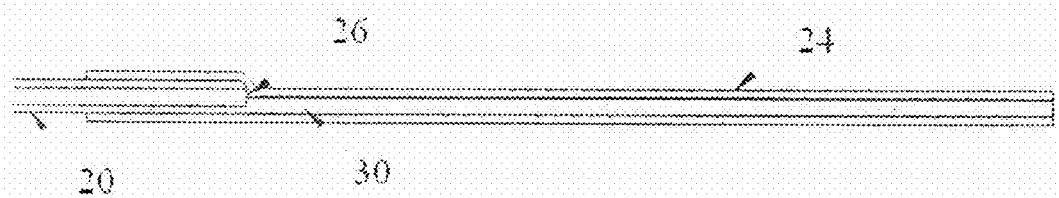
FIG. 8 depicts a longitudinal section of a spiral-forming balloon (deflated) having a stainless steel wire welded to the distal end of a stainless steel conduit.

In a further reduced cross-section variant, shown in FIG. 8, a stainless steel wire 30 having a diameter of, for example, 0.2 mm may be welded to the distal end of the tube 20. As a result of this modification, a balloon 24 with a smaller ID may be used, thereby leading to a distal section having a significantly smaller cross section profile.

Figure 9:
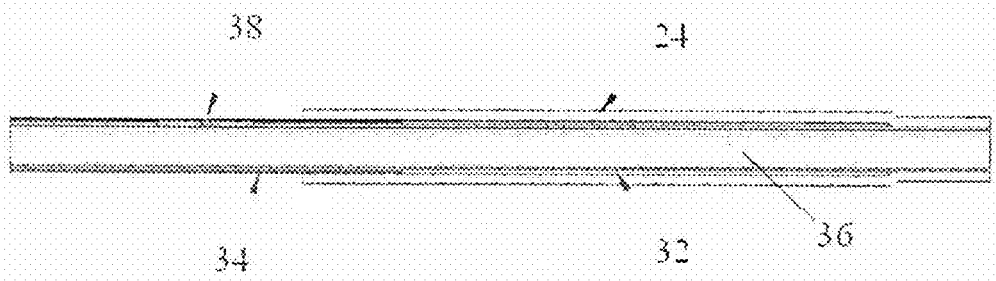
FIG. 9 depicts a longitudinal section of a spiral-forming balloon (deflated) featuring a side-hole for the injection of contrast agents, thrombolytic agents or other fluids.

In another preferred embodiment of the invention, the catheter may be delivered (in either over-the-wire or rapid exchange mode) over a coronary 0.014" guidewire (FIG. 9). The minimum cross sectional profile of the catheter may be in the order of 0.8-1.0 mm. The balloon 24 depicted in the longitudinal section shown in FIG. 9 is mounted in a conventional manner on a two-conduit coaxial design catheter similar to standard balloon catheters known in art, with the proximal end of the balloon 24 being attached to the outer tube 34 and the distal end thereof being attached to the inner tube 32.

Both the inner tube and the outer tube may be constructed by the use of extrusion techniques from materials commonly used in the art including Nylon, Pebax, PET and Polyurethane. The balloon 24 is inflated in a conventional manner well known to skilled artisans in the field, through an inflation lumen formed by the space between the inner and outer tubes.

In most over-the-wire catheters, the lumen of the inner conduit functions primarily as a guidewire lumen. However, in the embodiments illustrated in FIGS. 9 to 11, the presence of one or more side exits (or apertures) 38 proximal to the balloon that communicate between said guidewire lumen 36 and the area surrounding the outer tube permit said lumen to be additionally used for the delivery of liquid substances of various types to the region of the blood vessel that is in proximity to said exit(s). Thus, in one preferred embodiment, after the balloon is delivered to the target and the guidewire withdrawn, the guidewire lumen may used for injecting liquids (including, but not limited to standard contrast media and thrombolytic agents, such as tPA) through both the side exit and distal exit of the lumen. In other preferred embodiments, fluid injection takes place while the guidewire is still indwelling.

The aforementioned side aperture 38 will generally be sized such that its surface area will be approximately equal to the cross-sectional area of the inner tube lumen. The aperture is formed by means of a laser cut, and the side walls of said aperture are sealed by thermo-bonding methods, in order to prevent seepage between the inner and outer tubes.

Figure 10:
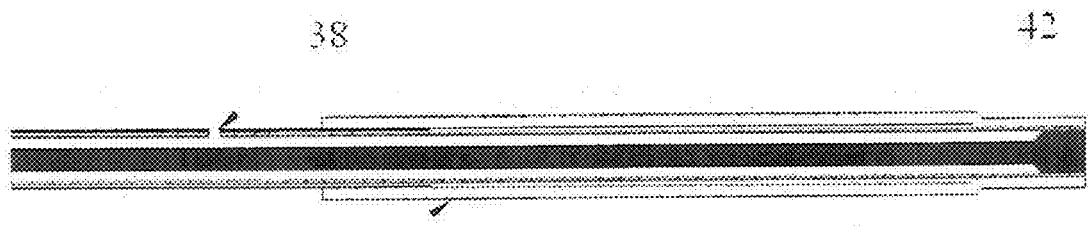
FIG. 10 shows a longitudinal section of an embodiment of the present invention in which a specially-designed guidewire is used to block the distal catheter exit.
Figure 10:
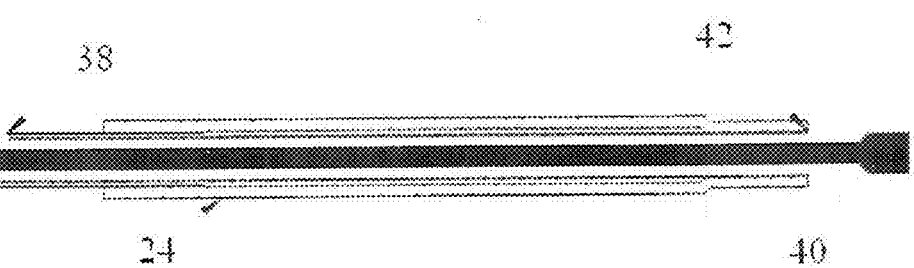
Figure 11:
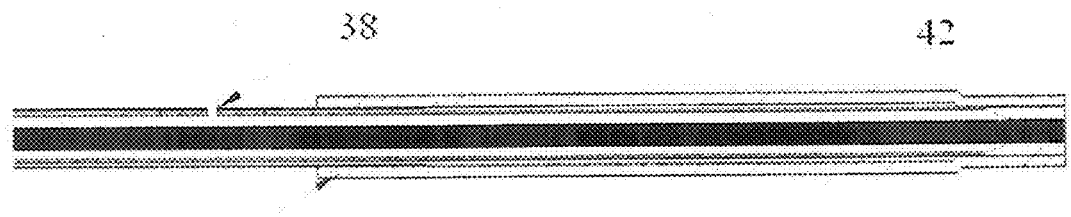
FIG. 11 shows a longitudinal section of an alternative embodiment of the device of the present invention, in which the inner catheter lumen has a narrowed distal end, thereby allowing the distal catheter exit to be blocked by a standard guidewire.
Figure 11:
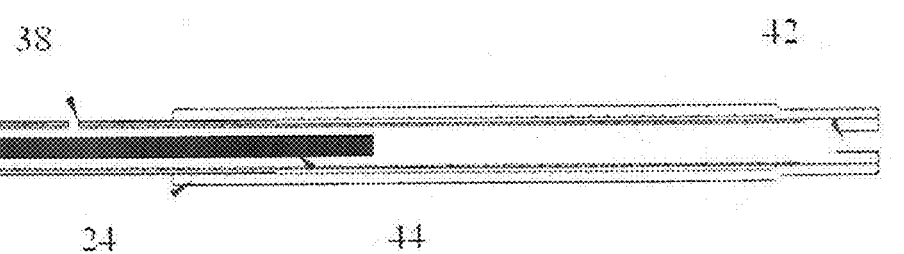

In the case of injection of thrombolytic agents through the catheter it is of utmost importance to avoid injecting said agents on the distal side of the balloon. In order to prevent this occurrence, the distal opening of the catheter needs to be capable of being blocked, while the side exit remains open. Moreover, injection of thrombolytic agents proximal to the balloon, and in the vicinity of the thrombus (by the aforementioned means of blocking the distal opening while retaining the side aperture open) beneficially enhances the dissolution of the thrombus. While several different technical solutions may be employed in order to achieve closure of the distal opening, while retaining an open side aperture, the following designs represent particularly preferred embodiments:

i. FIG. 10 illustrates the use of a specially-designed graded guidewire 40 having a wider distal end that is used to block the distal exit 42, thus permitting flow through the proximal exit 38 only. The upper part of FIG. 10 illustrates this embodiment with the distal exit 42 blocked, while the lower part of the figure shows said exit in the open position.
  ii. FIG. 11 shows the use of a specially-modified catheter inner lumen which has a narrowed distal exit 42 so that a standard 0.014" guidewire 44 can block the distal exit, allowing flow through the proximal exit 38 only. When the guidewire is retrieved about 10 cm backward, flow is possible through both the side exit 38 and the distal exit 42. The upper part of FIG. 11 illustrates this embodiment with the distal exit 42 blocked, while the lower part of the figure shows said exit in the open position.

The conduits used to construct the catheter device of the present invention may be made of any suitable material including (but not limited to) a biocompatible polymer such as polyurethane or nylon or PET, or a biocompatible metal such as stainless steel, and may be manufactured utilizing conventional methods, such as extrusion and laser cutting. The diameter of the conduits is generally in the range of 0.5-2.0 mm, and their length is generally in the range of 100-2000 mm.

The compliant balloon may be inflated by introducing a pressurized inflation media via an inflation fluid port that is in fluid connection with a source of pressurized media and a pumping device or syringe. In the case of a single conduit catheter, the inflation media passes through openings in the wall of the catheter shaft located between the proximal and distal attachment points of the balloon. In the case of a dual (inner-outer) conduit conformation, as described above, the inflation media passes via an inflation fluid lumen formed between the inner wall of the outer conduit and the outer surface of the inner conduit.

In another embodiment, the balloon of the present invention may be assembled onto a two-conduit catheter, wherein the inner conduit is movable in relation to the outer conduit. In this way, the cross-sectional profile of the non-inflated balloon may be reduced even further by means of moving the inner tube distally prior to insertion of the catheter into the vasculature, thereby stretching the balloon and thus reducing its wall thickness.

Typical Procedure for Using a Balloon Catheter of the Present Invention (Fitted with an Aspiration Tube) to Remove Thrombotic Material from a Blood Vessel:
1. The catheter is advanced through the target blood vessel until the balloon is brought close to the region of the thrombotic material that is to be removed.
2. The balloon is inflated, a spiral channel thereby being formed between the outer surface of balloon (which has now adopted a spiral or helical form) and the blood vessel wall. This channel fills with particulate thrombotic matter, which becomes compressed and elongated as a result of the pressure exerted by the expanded balloon on the blood vessel wall.
3. A negative pressure source is connected to the proximal end of the aspiration tube, and the compressed, elongated thrombotic material is thereby aspirated into said tube.
4. The balloon may then optionally be partially or completely deflated and moved into proximity with a further aspiration target, and steps 2 and 3 repeated.
5. When the clinical need is met, the spiral balloon is completely deflated and retrieved from the body.

The pressure in the balloon when fully inflated with an expansion medium such as saline or a contrast medium is in the range of 0.5-4 atmospheres, and often in the range of 1.5-2 atmospheres.

It is, of course, to be recognized that the spiral-forming balloon catheter of the present invention has many different applications, in addition to the use in thrombus removal described above. For example, the expanded spiral balloon may be used for anchoring a catheter (or other elongate device) within a blood vessel, without blocking blood flow in the region of the anchoring balloon.

In addition, in other applications, the spiral balloon may be used for the purpose of cooling or heating tissue or blood in the immediate vicinity of said balloon.

In another aspect, the balloon may be covered or partly covered with a network of thin filaments, thereby creating a distal protection element, which may serve to enhance the ability of the spiral balloon to trap thrombotic material during withdrawal of the catheter.

A further application for the spiral-forming balloon of the present invention is in the treatment and/or remodeling of vascular aneurysms (including, but not limited to, cerebral aneurysms). Prior art methods of treatment generally use an inflated catheter balloon as a 'floor' or base during the insertion of coils into the aneurysm that is being re-modeled. However, one drawback of the use of conventional balloons in this situation is that blockage (total or near-total) of blood flow in the region of the aneurysm. This blockage may clearly have serious negative implications, particularly when dealing with a cerebral aneurysm. The use of a spiral-forming balloon of the present invention, however, permits blood flow to continue through and around the spiral channels, thereby preventing ischemic and hypoxic damage to sensitive tissues distal to the treatment site.

In a further modification of the methods of use disclosed and described hereinabove, following insertion of the catheter system of the present invention into the body, and its arrival at the intended working site, said catheter may be left in situ for periods of up to several hours, in order perform its various functions (e.g. thrombus collection) as a temporary indwelling device.

In a further aspect, the present invention provides a two-balloon embodiment of the catheter device, wherein an inner compliant balloon (as described hereinabove) is fitted over a conduit and covered with a second, outer non-compliant or semi-compliant balloon. In its deflated state (FIG. 12), the inner balloon is in the form of a tube of compliant material with a diameter, in one preferred embodiment, of up to $\frac{1}{15}$ of the final crossing profile of the inflated balloon. The tube can be constructed with a uniform wall thickness or with a wall thickness which varies along its length. The collapsed inner balloon together with the outer balloon that surrounds it are jointly indicated in FIG. 12 by part number 112 attached to catheter shaft 110.

The inner balloon can be made from one material. Alternatively, the inner balloon may be constructed from two or more different materials, thereby producing a non-uniform spiral balloon upon inflation. Suitable materials for use in constructing the inner balloon include (but are not limited to): silicones and thermoplastic elastomers (TPEs).

Figure 13:
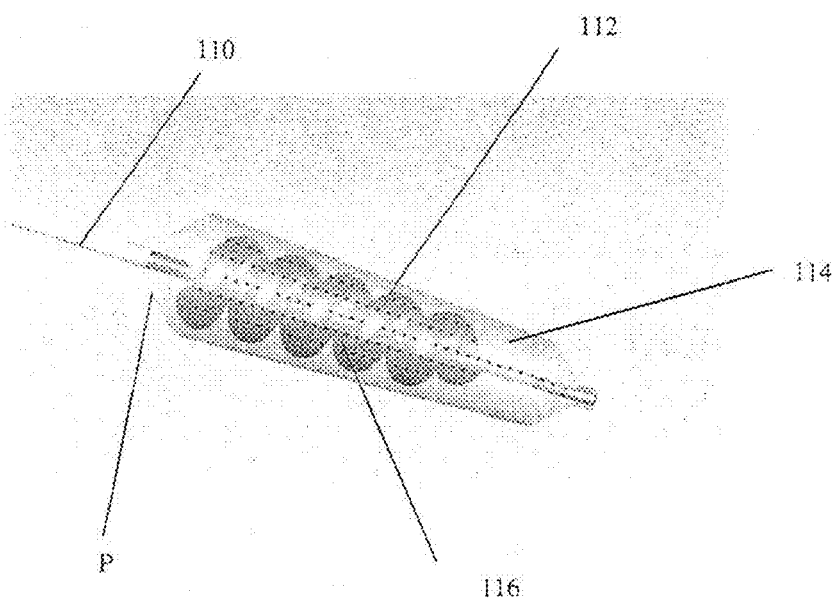
FIG. 13 illustrates the balloon catheter of the embodiment of the present invention depicted in FIG. 12, following the first stage of inflation of the spiral balloon.
Figure 14:
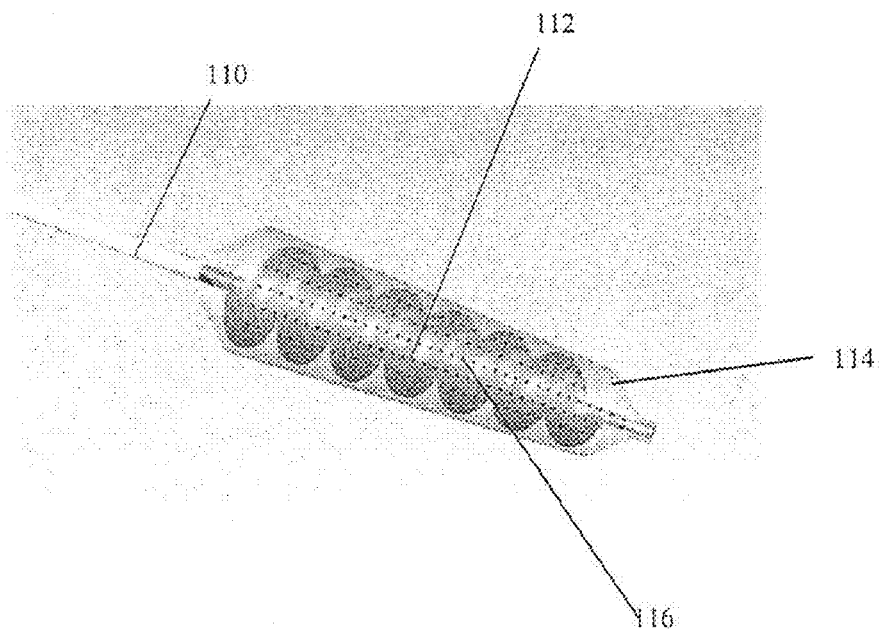
FIG. 14 illustrates the balloon catheter of the embodiment of the present invention depicted in FIG. 12, following full inflation of the spiral balloon.

The inner balloon 112 is bound at two points to a rigid or semi-rigid conduit 110 which is threaded through the balloon. Since the inner balloon is made of a compliant material it elongates during inflation. However, as the inner balloon 112 is bound at both its ends, its longitudinal elongation is restrained. Provided certain balloon-related design parameter criteria are met (as discussed hereinabove), said inner balloon 112 will then buckle and assume a spiral shape as shown in FIGS. 13 and 14. As seen in these figures, the outer balloon 114 (perforated with small pores 116) completely surrounds the inner balloon 112. The proximal end of the outer balloon is indicated by the letter P in FIG. 13.

Typically, the inner balloon has a length in the range of 15 mm to 50 mm and a wall thickness in the range of 100 micron to 400 micron. It should be emphasized that the preceding dimensions (and all other dimensions that appear herein) are exemplary values only, and should not be construed as limiting the size of the presently-disclosed device in any way.

Figure 15:
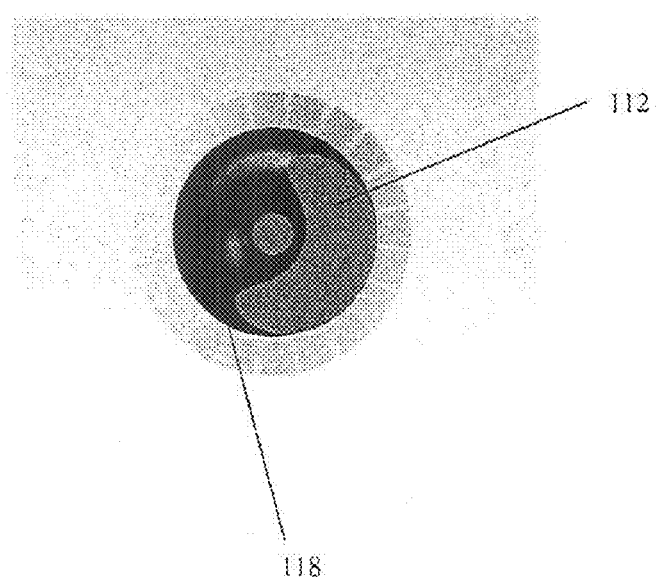
FIG. 15 shows a short-axis cross section of the balloon catheter shown in FIG. 13, with the spiral balloon in its partially inflated state.
Figure 16:
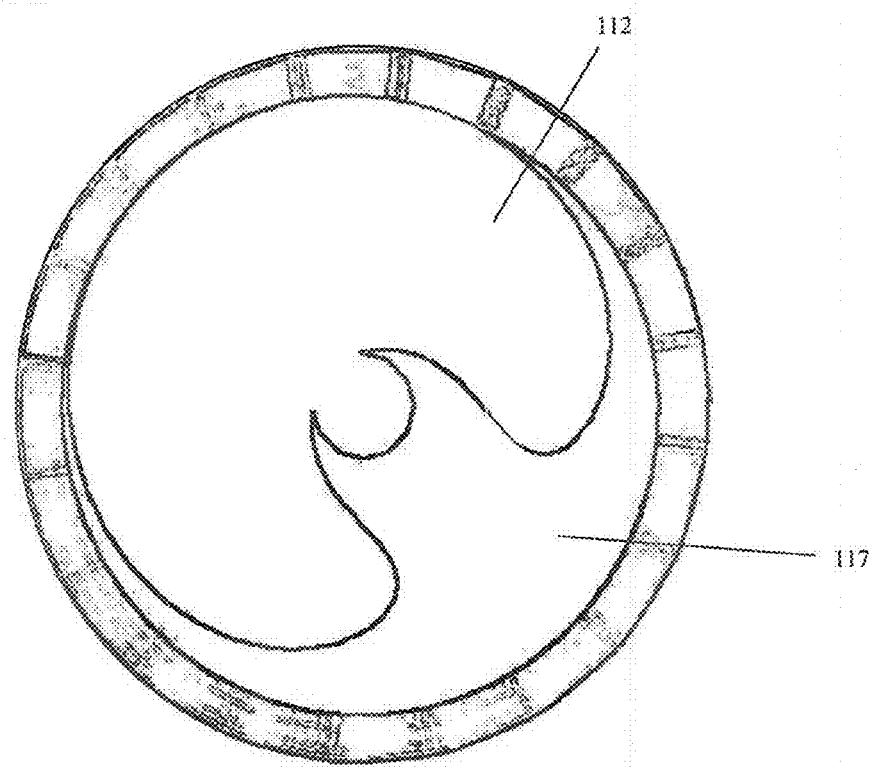
FIG. 16 shows a short-axis cross section of the balloon catheter of the present invention shown in FIG. 14, with the spiral balloon almost fully inflated.

The inner, spiral balloon 112 in its inflated state creates a spiral channel 117 surrounding it, which allows free flow through the channel. The shape and size of the cross-section of the spiral channel 117 can be varied from a very small cross-section area (when the balloon is fully inflated, FIG. 16) to 70-80% (when partially inflated, FIG. 15) of the balloon cross-section area.

The spiral balloon is covered with a non-compliant or semi-compliant balloon which is bound to the same shaft as the spiral balloon.

The outer balloon may be constructed of any suitable non-compliant or semi-compliant material, including (but not limited to): nylon, Pebax, polyurethane and polyethylene terephthalate (PET).

Figure 17:
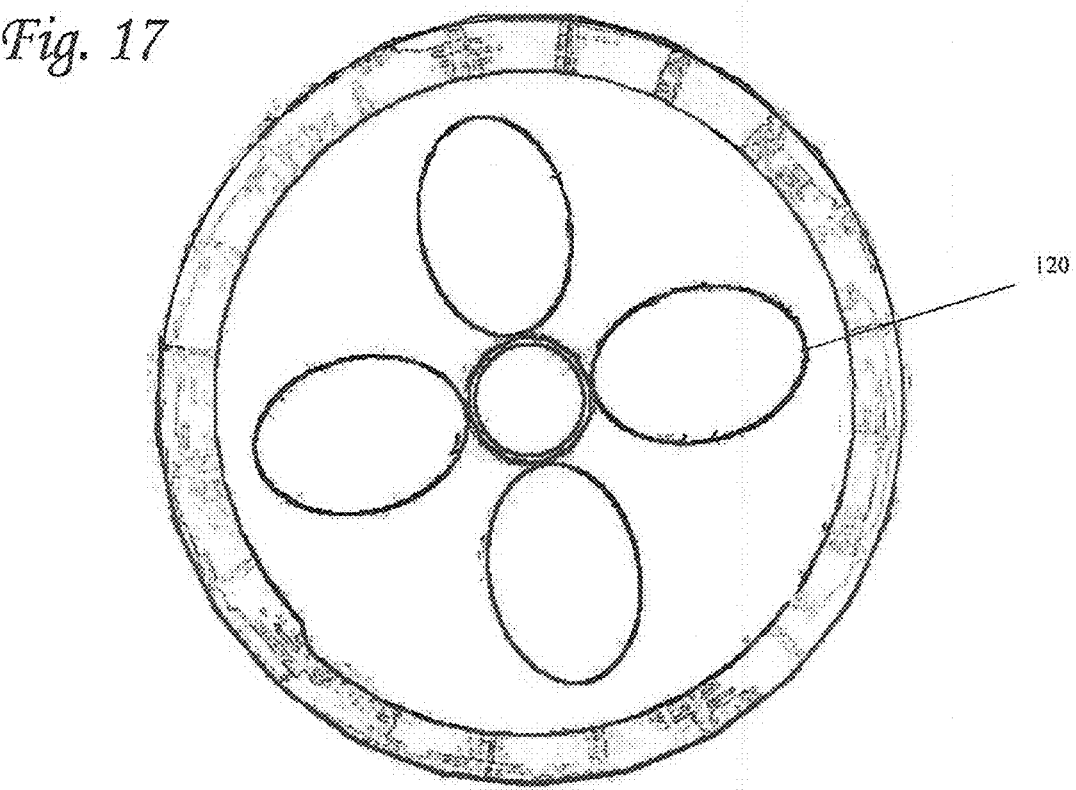
FIG. 17 represents a short-axis cross section of the balloon catheter of the present invention shown in FIG. 12, at the proximal end of the spiral balloon.

The outer balloon is perforated along most of its lateral surface by a first set of holes or pores 116 (FIG. 13) of a pre-determined size, whereas a second set of pores 120 perforates the proximal taper or neck of said outer balloon, said pores 120 being fewer in number but having a larger diameter than the holes of the aforementioned first set (FIG. 17). When the inner balloon is in its deflated state, the outer balloon is folded on top of the spiral balloon to create a reduced cross-section profile. Upon active inflation of the inner balloon, the outer balloon passively expands as a result of the outward pressure exerted by the inflated or partially inflated spiral balloon.

Figure 12:
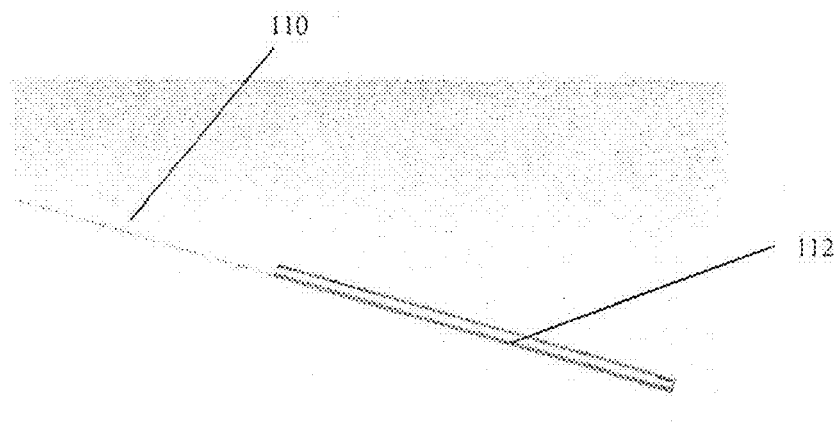
FIG. 12 depicts the balloon catheter of a further preferred embodiment of the present invention having inner and outer balloons, shown here in their collapsed, deflated states.

The general embodiment of this embodiment of the balloon catheter of the present invention that is described immediately hereinabove and depicted in FIGS. 12-14 comprises a single catheter conduit to which is attached both the inner and outer balloons. However, it is to be recognized that many other catheter conduit conformations may also be used in the present invention. For example, instead of the single-conduit system, the device of the present invention may have a two-conduit conformation, with (for example) the proximal necks of the inner and outer balloons being attached to the outer surface of an outer conduit, while the distal necks thereof are attached to the outer surface of an inner conduit that is disposed within the lumen of said outer conduit. In this type of conformation, the inner conduit will generally extend beyond the distal end of the outer conduit. The device of the present invention may also comprise one or more conduits having multiple lumens (e.g. bi-lumen catheters) where the additional lumens may be used for a variety of purposes, including the passage of guidewires, instrumentation or tools.

In addition, various catheter tubes having a particularly small cross-sectional profile may be used to mount the spiral-forming balloon of the present invention. Examples of such small profile catheter tubes are described hereinabove, in relation to other embodiments of the device of the present invention. Such small profile tubes may also be used in conjunction with the presently-described, two-balloon device. Similarly, the various catheter tubes fitted with one or more lateral apertures (for the purpose of fluid injection), which were described hereinabove, are also intended for use with the two-balloon device.

The conduits used in this embodiment of the catheter device of the present invention may be made of any suitable material including (but not limited to) a biocompatible polymer such as polyurethane or nylon or PET, or a biocompatible metal such as stainless steel, and may be manufactured utilizing conventional methods, such as extrusion and laser cutting. The diameter of the conduits is generally in the range of 0.5-2.0 mm, and their length is generally in the range of 100-2000 mm.

The compliant inner balloon may be inflated by introducing a pressurized inflation media via an inflation fluid port that is in fluid connection with a source of pressurized media and a pumping device or syringe. In the case of a single conduit catheter, the inflation media passes through openings in the wall of the catheter shaft located between the proximal and distal attachment points of the balloon. In the case of a dual (inner-outer) conduit conformation, as described above, the inflation media passes via an inflation fluid lumen formed between the inner wall of the outer conduit and the outer surface of the inner conduit.

Typical Procedure for Using the 2-Balloon Embodiment of the Device of the Present Invention:

1. The catheter is advanced through the target blood vessel until the balloons are delivered distally to the aspiration target.
2. The inner balloon is partially inflated to a first pressure and the outer balloon passively expands and spreads over said inner balloon. A spiral channel is formed between the inner balloon (which has now adopted a spiral or helical form) and the outer balloon. This channel fills with both particulate matter and blood situated proximal to the balloon through the large openings located in the proximal taper of the outer balloon. The presence of the smaller pores along most of the lateral surface of the outer balloon, together with the formation of the aforementioned spiral channel, permits continued blood flow in the vessel. The outer balloon functions as a filter and traps debris within the spiral cavity.
3. Further inflation of the balloon causes the proximal coils of the spiral balloon to block the large openings located at the proximal neck of the outer balloon and reduce the volume of the spiral channel, thereby squeezing a portion of the material through the small perforations in the outer balloon.
4. Partial deflation recreates the spiral channel which continues to fill with new portions of matter (blood and particulate matter).
5. Step 3 and 4 can be repeated several times.
6. When the clinical need is met, the spiral balloon is completely deflated and retrieved through the guiding catheter and the debris is trapped inside the outer balloon.

By way of further explanation, it should be noted that the filtering and trapping function of the outer balloon mentioned and described in steps 2 and 3, above, is related to the size of the pores formed along most of the surface of the outer balloon ("small pores"), as well as the size of the larger pores situated at the proximal neck of the outer balloon ("large pores"). Thus, particulate matter having an average diameter less than the average diameter of the large pores will be able to enter the space between the inner and outer balloons. Any particles larger than the size of these pores will not be able to enter into that space. Once inside the space between the inner and outer balloons, and following the further expansion of the inner balloon and blockage of the large pores described in step 3, above, any particles smaller than the small pores will be squeezed out through said small pores and thereby returned to the bloodstream. Conversely, all particles larger than the small pore diameter will be retained in the space between the outer and inner balloons and ultimately removed from the body together with the catheter. It will therefore be appreciated that the outer balloon performs the following three key functions:

filtration of solid or semi-solid particles suspended in blood;
  pumping of the blood and particulate matter smaller than the small pores back into the bloodstream; and
  entrapment of large debris having a size greater than the small pores.

The pressure in the balloon after partial inflation to a first expanded state (as described in step 2, above) is in the range of 0.5 to 10 atmospheres.

All of the abovementioned parameters are given by way of example only, and may be changed in accordance with the differing requirements of the various embodiments of the present invention. Thus, the abovementioned parameters should not be construed as limiting the scope of the present invention in any way.

EXAMPLE

Influence of Key Balloon Parameters on their Ability to Adopt a Spiral Conformation The following table summarizes certain key parameters of a series of different compliant balloons which were bound at both ends to a rigid catheter (diameter 0.3 mm). In the cases in which a spiral conformation was not achieved following inflation with water, this fact is mentioned in the 'comments' column of the table:

| Balloon Material | % Elongation at break | OD [mm] | ID [mm] | $L_0$ [mm] | Number of Threads (N) | Spiral Balloon OD [mm] | Comments |
|---|---|---|---|---|---|---|---|
| TPE* | 510 | 0.8 | 0.4 | 20 | 3 | 4.5 | |
| TPE | 510 | 0.9 | 0.5 | 20 | 3 | 5.5 | |
| TPE | 700 | 0.8 | 0.4 | 20 | 2.5 | 7.5 | |
| Silicone | 373 | 0.8 | 0.4 | 20 | 4 | 4 | |
| Silicone | 373 | 0.6 | 0.3 | 20 | N/A | N/A | Spiral balloon was not formed due to no space between the ID of the balloon and the OD of the shaft. |
| Silicone | 373 | 0.8 | 0.4 | 7 | N/A | N/A | A spiral balloon was not formed. The initial length was too short. |
| Polyurethane | 50 | 0.8 | 0.4 | 20 | N/A | N/A | A spiral balloon was not formed due to an elongation which was too low. |

*The TPE used in this study was Evoprene Super G 948 (Alpha Gary Company)

It will be seen from the proceeding table that only the balloons characterized by having certain structural parameters (e.g. length, diameter, material etc.) are capable of adopting a spiral conformation upon inflation.

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. A method for removing particulate matter from a body passage in a patient in need of such treatment, comprising the steps of:
    a) providing a catheter fitted with a compliant balloon and an aspiration element, said balloon having a non-helical shape and surrounding said catheter in a non-spiral manner in its deflated state, wherein said balloon is constructed such that it is capable of adopting a spiral or helical conformation upon inflation based upon an intrinsic ability of the balloon;
    b) introducing said catheter into a peripheral blood vessel and advancing same until said balloon is located in the region of the particulate matter to be removed;
    c) inflating said balloon such that it adopts the spiral or helical conformation, thereby causing said particulate matter to enter a spiral channel thus formed in the external surface of the balloon, and to become squeezed and elongated between said balloon and said blood vessel wall;
    d) aspirating said squeezed particulate matter into said aspiration element, wherein said aspiration may be performed continuously or intermittently;
    e) optionally partially or completely deflating the balloon and re-locating the catheter such that said balloon becomes located in another region of particulate matter to be removed, and repeating steps (c) and (d);
    f) completely deflating the balloon and withdrawing the catheter from the patient's vasculature.

2. The method according to claim 1, wherein the particulate matter to be removed is thrombotic material.

3. The method according to claim 1, wherein the intrinsic ability is a function of one or more of materials used in construction of said balloon, dimensions of said balloon, and attachment of said balloon at each of its ends to a catheter shaft.

4. A method for removing particulate matter from a body passage in a patient in need of such treatment, comprising the steps of:
    a) providing a catheter system comprising one or more conduits to which are attached an inner compliant balloon, the inner balloon being enclosed by an outer non-compliant or semi-compliant balloon, and the inner balloon having a non-helical shape and surrounding said catheter in a non-spiral manner in its deflated state, wherein said inner balloon is constructed such that it is capable of adopting a spiral or helical conformation upon inflation based upon an intrinsic ability of the inner balloon, and wherein the outer balloon of said catheter system is perforated by a first set of pores along most or all of its surface, and is further perforated by a second set of pores or openings at the proximal neck thereof, wherein the pores of said second set are significantly fewer in number and larger in diameter than said first set;
    b) introducing said catheter into a peripheral blood vessel and advancing same until the balloons are located in the region of the particulate matter to be removed;
    c) partially inflating the inner balloon to a first expanded state such that the inner balloon adopts a spiral conformation and such that a spiral channel is formed between said spiral balloon and the outer balloon, said channel becoming filled with particulate matter that has entered said spiral channel through said second set of pores;
    d) further inflating the inner balloon to a second expanded state, such that the proximal coils of the spiral-shaped inner balloon block the second set of pores and reduce the volume of the spiral channel formed in step (c), thereby causing the outward passage of particulate matter of a size smaller than the average diameter of the first set of pores through said pores, but retaining particulate matter of particulate matter of a size larger than said average diameter in the reduced space between the inner and outer balloons;

e) partially deflating the inner balloon to the first expanded state described in step (c), such that further particulate matter may be received in the spiral channel;

f) repeating steps (d) and (e) as required; and g) completely deflating the inner balloon and withdrawing the catheter from the patient's vasculature with the particulate matter trapped between the inner and outer balloons.

5. The method according to claim 4, wherein the particulate matter to be removed is thrombotic material.

6. The method according to claim 4, wherein the intrinsic ability is a function of one or more of materials used in construction of said balloon, dimensions of said balloon, and attachment of said balloon at each of its ends to a catheter shaft.

7. A method for removing thrombotic material from a body passage in a patient in need of such treatment, comprising the steps of:
   a) providing a catheter fitted with a compliant balloon, said balloon having a non-helical shape and surrounding said catheter in a non-spiral manner in its deflated state, wherein said balloon is constructed such that it is capable of adopting a spiral or helical conformation upon inflation based upon an intrinsic ability of the balloon;
   b) introducing said catheter into a peripheral blood vessel and advancing same until said balloon is located in the region of the thrombotic material to be removed;
   c) inflating said balloon such that it adopts the spiral conformation having a spiral channel winding around the external surface of said balloon, thereby causing said thrombotic material to enter a spiral channel and to become squeezed and elongated between said balloon and said blood vessel wall;
   d) deflating said balloon, thereby creating a space between the deflated balloon and the squeezed thrombotic material, into which a thrombolytic agent may be introduced, thereby enhancing thrombo-dissolution;
   e) rapidly repeating steps (c) and (d); and
   f) completely deflating the balloon and withdrawing the catheter from the patient's vasculature.

8. The method according to claim 7, wherein the relative values of the length of the balloon in the deflated state, the elongation fraction and the inner diameter of said balloon in the deflated state are chosen, such that said balloon is capable of adopting a spiral or helical conformation upon inflation.

9. The method according to claim 7, wherein the balloon is attached to a single catheter conduit.

10. The method according to claim 7, wherein a distal neck of the balloon is attached to one catheter conduit while a proximal neck thereof is attached to a second conduit, wherein said first and second conduits are arranged such that at least a portion of the shaft of one of the conduits is disposed within the lumen of the other conduit.

11. The method according to claim 7, wherein the balloon forms the spiral or helical shape in the inflated state without use of ancillary structures.

12. The method according to claim 7, wherein the intrinsic ability is a function of one or more of materials used in construction of said balloon, dimensions of said balloon, and attachment of said balloon at each of its ends to a catheter shaft.

13. A method for removing a thrombus from a body passage in a patient in need of such treatment, comprising the steps of:
   a) providing a catheter fitted with a compliant balloon, said balloon having a non-helical shape and surrounding said catheter in a non-spiral manner in its deflated state, wherein said balloon is constructed such that it is capable of adopting a spiral or helical conformation upon inflation based upon an intrinsic ability of the balloon;
   b) introducing said catheter into a peripheral blood vessel and advancing same until said balloon is located in the region of the thrombus to be removed;
   c) trapping the thrombus within a spiral channel formed by inflation of the balloon; and
   d) withdrawing the catheter through the vasculature and out of the body, together with said entrapped thrombus.

14. The method according to claim 13, wherein the relative values of the length of the balloon in the deflated state, the elongation fraction and the inner diameter of said balloon in the deflated state are chosen, such that said balloon is capable of adopting a spiral or helical conformation upon inflation.

15. The method according to claim 13, wherein the balloon is attached to a single catheter conduit.

16. The method according to claim 13, wherein a distal neck of the balloon is attached to one catheter conduit while a proximal neck thereof is attached to a second conduit, wherein said first and second conduits are arranged such that at least a portion of the shaft of one of the conduits is disposed within the lumen of the other conduit.

17. The method according to claim 16, wherein said catheter further comprises at least one side aperture that connects a lumen of the inner conduit with a space surrounding the outer conduit.

18. The method according to claim 13, wherein the balloon forms the spiral or helical shape in the inflated state without use of ancillary structures.

19. The method according to claim 13, wherein the intrinsic ability is a function of one or more of materials used in construction of said balloon, dimensions of said balloon, and attachment of said balloon at each of its ends to a catheter shaft.

20. The method according to claim 13, wherein said catheter further comprises an aspiration tube, a distal end of which is located close to, and on the proximal side of, a proximal neck of the balloon.

* * * * *